(12) United States Patent
Wapner et al.

(10) Patent No.: US 10,939,944 B2
(45) Date of Patent: Mar. 9, 2021

(54) REMOVABLE ORTHOPEDIC SCREWS

(71) Applicant: GLW, Inc., Waxhaw, NC (US)

(72) Inventors: Peter Wapner, Philadelphia, PA (US); Charles Wapner, Washington, DC (US); Stefan Voelzow, Mönkeberg (DE); Axel Cremer, Fahrenkrug (DE)

(73) Assignee: GLW, Inc., Waxhaw, NC (US)

( * ) Notice: Subject to any disclaimer, the term of this patent is extended or adjusted under 35 U.S.C. 154(b) by 63 days.

(21) Appl. No.: 16/387,799

(22) Filed: Apr. 18, 2019

(65) Prior Publication Data

US 2019/0321087 A1      Oct. 24, 2019

Related U.S. Application Data

(60) Provisional application No. 62/659,340, filed on Apr. 18, 2018.

(51) Int. Cl.
*A61B 17/86* (2006.01)
*A61B 17/88* (2006.01)

(52) U.S. Cl.
CPC ........ *A61B 17/8605* (2013.01); *A61B 17/866* (2013.01); *A61B 17/8625* (2013.01); *A61B 17/8886* (2013.01); *A61B 17/864* (2013.01)

(58) Field of Classification Search
CPC .............. A61B 17/8605; A61B 17/861; A61B 17/8615; A61B 17/8625; A61B 17/863; A61B 17/8635; A61B 17/864; A61B 17/8645
See application file for complete search history.

(56) References Cited

U.S. PATENT DOCUMENTS

| 4,776,328 | A | 10/1988 | Frey et al. |
| 5,375,956 | A | 12/1994 | Pennig |
| 5,536,127 | A | 7/1996 | Pennig |
| 6,001,101 | A | 12/1999 | Augagneur et al. |
| 6,306,140 | B1 | 10/2001 | Siddiqui |
| 6,319,254 | B1 * | 11/2001 | Giet ..................... A61B 17/863 606/104 |
| 6,355,043 | B1 | 3/2002 | Adam |

(Continued)

FOREIGN PATENT DOCUMENTS

| CN | 208355547 | 1/2019 |
| DE | 102009033138 | 2/2011 |

(Continued)

OTHER PUBLICATIONS

ACUMED. "Acutrak Screw Removal Technique," retrieved from Internet Mar. 8, 2018, pp. 1-12.

(Continued)

*Primary Examiner* — Anu Ramana
(74) *Attorney, Agent, or Firm* — MacMillan, Sobanski & Todd, LLC (57) ABSTRACT

The disclosure relates to medical devices and methods of manufacturing medical devices. An orthopedic screw includes a shaft having a proximal end, a distal end, a body extending between the proximal end and the distal end, and a longitudinal axis. A distal thread on an external surface of the shaft extends around the longitudinal axis. A head portion includes a series of cutting teeth that lie on a plane that is perpendicular to the longitudinal axis of the shaft. A distal tip portion defines a cutting edge.

20 Claims, 5 Drawing Sheets

(56) References Cited

U.S. PATENT DOCUMENTS

| | | |
|---|---|---|
| 7,582,107 B2 * | 9/2009 | Trail ................ A61B 17/8635 606/304 |
| 8,062,270 B2 | 11/2011 | Sweeney |
| 8,118,849 B2 | 2/2012 | Wahl et al. |
| 8,142,190 B2 | 3/2012 | Anitua Aldecoa |
| 8,403,972 B2 | 3/2013 | Hasenböhler et al. |
| 8,636,808 B2 | 1/2014 | Olson |
| 9,220,602 B2 | 12/2015 | Olson |
| 9,314,286 B2 | 4/2016 | Bottlang et al. |
| 9,358,057 B1 | 6/2016 | Whipple et al. |
| 9,526,546 B2 | 12/2016 | Horwitz |
| 9,532,822 B2 | 1/2017 | Fang et al. |
| 9,636,158 B2 | 5/2017 | Fang et al. |
| 9,687,284 B2 | 6/2017 | Pancheco et al. |
| 9,757,168 B2 | 9/2017 | Seavey et al. |
| 9,848,927 B2 | 12/2017 | Giomo |
| 9,867,644 B2 | 1/2018 | Meng et al. |
| 2007/0233071 A1 * | 10/2007 | Dewey ................ A61B 17/866 606/250 |
| 2008/0027444 A1 | 1/2008 | Malek |
| 2008/0183220 A1 | 7/2008 | Glazer et al. |
| 2008/0208259 A1 | 8/2008 | Gilbert et al. |
| 2009/0248089 A1 * | 10/2009 | Jacofsky ............ A61B 17/7064 606/311 |
| 2010/0304335 A1 | 12/2010 | Garcia Saban et al. |
| 2011/0098756 A1 | 4/2011 | Brannon |
| 2011/0137354 A1 | 6/2011 | Biedermann et al. |
| 2012/0197311 A1 | 8/2012 | Kirschman |
| 2012/0226325 A1 | 9/2012 | Lyons et al. |
| 2012/0232599 A1 | 9/2012 | Schoenly et al. |
| 2013/0117985 A1 | 5/2013 | Siraky et al. |
| 2013/0245626 A1 | 9/2013 | Lavi et al. |
| 2014/0155943 A1 | 6/2014 | Andersen |
| 2014/0188239 A1 | 7/2014 | Cummings |
| 2014/0329202 A1 | 11/2014 | Zadeh |
| 2015/0201984 A1 | 7/2015 | Orbay et al. |
| 2016/0157854 A1 | 6/2016 | Sojka et al. |
| 2016/0166300 A1 | 6/2016 | Peukert et al. |
| 2016/0213413 A1 | 7/2016 | Hientzsch et al. |
| 2016/0235452 A1 | 8/2016 | Bourda et al. |
| 2016/0242820 A1 | 8/2016 | Whipple et al. |
| 2016/0287300 A1 | 10/2016 | McCormick et al. |
| 2016/0310187 A1 | 10/2016 | Leibinger et al. |
| 2017/0071646 A1 | 3/2017 | Horwitz |
| 2017/0105778 A1 | 4/2017 | Williams |
| 2017/0196612 A1 | 7/2017 | Castaneda et al. |
| 2018/0008317 A1 | 1/2018 | Sinha |

FOREIGN PATENT DOCUMENTS

| | | |
|---|---|---|
| EP | 2422714 | 10/2015 |
| FR | 2840799 | 6/2002 |
| FR | 3000662 | 1/2013 |
| FR | 3000664 | 1/2013 |
| JP | 2016-512094 | 4/2016 |
| WO | WO2000038586 | 7/2000 |
| WO | WO2004086991 | 10/2004 |
| WO | WO2008129401 | 10/2008 |
| WO | WO2010074714 | 7/2010 |
| WO | WO2010088213 | 8/2010 |
| WO | WO2013013218 | 1/2013 |
| WO | WO2013015754 | 1/2013 |
| WO | WO2013106217 | 7/2013 |
| WO | WO2013156816 | 10/2013 |
| WO | WO2013175099 | 11/2013 |
| WO | WO2014076157 | 5/2014 |
| WO | WO2014107503 | 7/2014 |
| WO | WO2015050900 | 4/2015 |
| WO | WO2015147847 | 10/2015 |
| WO | WO2017024277 | 2/2017 |
| WO | WO2017048826 | 3/2017 |
| WO | WO2017058965 | 4/2017 |
| WO | WO2017147537 | 8/2017 |

OTHER PUBLICATIONS

European Patent Office, International Search Report and Written Opinion for PCT application No. PCT/US2019/028046, dated Sep. 4, 2019, pp. 1-14.

European Patent Office, Provisional Opinion on Patentability for PCT application No. PCT/US2019/028046, dated Jul. 10, 2019, pp. 1-6.

* cited by examiner

REMOVABLE ORTHOPEDIC SCREWS

FIELD

The disclosure relates to the field of medical devices. More particularly, the disclosure relates to orthopedic screws. The disclosure also relates to methods of manufacturing orthopedic screws.

BACKGROUND

Orthopedic screws, also referred to as bone screws, are implantable medical devices that are commonly used for fracture stabilization and fixation. These devices can be made from a variety of materials and can include structural adaptations that facilitate their use and/or enhance their performance. For example, orthopedic screws having a variety of sizes, shapes, thread patterns, and head geometries are available.

It can be desirable or even necessary to remove an orthopedic screw after implantation, such as after bone consolidation has occurred. Changes in bony structures over time can make removal difficult; it is not uncommon for implanted bone screws that were clearly accessible at the time of implantation to have bone grown into the thread. Screws can even become completely overgrown with bone, making explantation extremely difficult. Use of accessory tools, such as coring bits and even impact drivers, can be necessary to initiate removal of screws in these situations.

A need remains, therefore, for improved removable orthopedic screws and methods of manufacturing orthopedic screws.

BRIEF SUMMARY OF SELECTED EXAMPLES

Various example orthopedic screws are described and illustrated herein.

An example orthopedic screw comprises a head portion defining a proximal end, a tip portion defining a cutting edge and a distal end, and a body extending between the proximal end and the distal end along a longitudinal axis and defining a distal thread extending around the longitudinal axis. The head portion defines a series of cutting teeth on a plane that is perpendicular to the longitudinal axis.

Another example orthopedic screw comprises a shaft having a proximal end, a distal end, and a body extending between the proximal end and the distal end along a longitudinal axis. The shaft has a shaft external surface that defines a distal thread extending around the longitudinal axis. A head portion is disposed on the shaft and defines a proximal thread and a series of cutting teeth lying on a plane that is perpendicular to the longitudinal axis of the shaft. The proximal thread is disposed between the distal thread and the series of cutting teeth and extends around the longitudinal axis. A tip portion is disposed on the shaft and defines a cutting edge. The proximal thread has a first outer diameter and the proximal end has a second outer diameter that is less than the first outer diameter.

Another example orthopedic screw comprises an inner core member defining a proximal end, a distal end, and a body extending between the proximal end and the distal end along a longitudinal axis. The proximal end defines a series of cutting teeth on a plane that is perpendicular to the longitudinal axis and the distal end defines a cutting edge. An outer body member is disposed circumferentially around the inner core member and defines a distal thread extending around the longitudinal axis.

Another example orthopedic screw comprises a shaft having a proximal end, a distal end, a body extending between the proximal end and the distal end, and a longitudinal axis, the shaft having a shaft external surface defining a distal thread that extends around the longitudinal axis; a head portion on the shaft, the head portion defining a proximal end defining a series of cutting teeth on a plane that is perpendicular to the longitudinal axis of the shaft; and a tip portion on the shaft, the tip portion defining a cutting edge.

Another example orthopedic screw comprises a shaft having a proximal end, a distal end, a body extending between the proximal end and the distal end, and a longitudinal axis, the shaft having a shaft external surface defining a distal thread that extends around the longitudinal axis; a head portion on the shaft, the head portion defining a proximal thread and a series of cutting teeth lying a on a plane that is perpendicular to the longitudinal axis of the shaft, the proximal thread disposed between the distal thread and the series of cutting teeth and extending around the longitudinal axis; and a tip portion on the shaft, the tip portion defining a cutting edge. The proximal thread has a first outer diameter and the proximal end has a second outer diameter that is less than the first outer diameter.

Another example orthopedic screw comprises a shaft having a proximal end, a distal end, a body extending between the proximal end and the distal end, and a longitudinal axis, the shaft having a shaft external surface defining a distal thread that extends around the longitudinal axis; a head portion on the shaft, the head portion defining a proximal thread and a series of cutting teeth lying on a plane that is perpendicular to the longitudinal axis of the shaft, the proximal thread disposed between the distal thread and the series of cutting teeth and defining a series of reverse cutting teeth in the first rotation of the proximal thread relative to the proximal end; and a tip portion on the shaft, the tip portion defining a cutting edge. The proximal thread has a first outer diameter and the proximal end has a second outer diameter that is less than the first outer diameter.

Various example methods of manufacturing an orthopedic screw are described.

An example method of manufacturing an orthopedic screw comprises machining a member from a precursor to form a distal thread on an external surface of the member between proximal and distal ends of the member and forming a series of cutting teeth on the proximal end of the member such that the series of cutting teeth lies on a plane that is parallel to the longitudinal axis of the member.

Another example method of manufacturing an orthopedic screw comprises machining a member from a precursor to form a distal thread on an external surface of the member between proximal and distal ends of the member; forming a series of cutting teeth on the proximal end of the member such that the series of cutting teeth lies on a plane that is parallel to the longitudinal axis of the member; and forming a proximal thread on the external surface of the member at an axial position between the distal thread and the proximal end of the member.

Another example method of manufacturing an orthopedic screw comprises machining a member from a precursor to form a distal thread on an external surface of the member between proximal and distal ends of the member and forming a proximal thread on the external surface of the member at an axial position between the distal thread and the proximal end of the member such that the proximal thread includes a reverse cutting tooth in the first rotation of the proximal thread.

Another example method of manufacturing an orthopedic screw comprises machining a member from a precursor to form a distal thread on an external surface of the member between proximal and distal ends of the member; forming a proximal thread on the external surface of the member at an axial position between the distal thread and the proximal end of the member such that the proximal thread includes a reverse cutting tooth in the first rotation of the proximal thread; and forming a series of cutting teeth on the proximal end of the member such that the series of cutting teeth lies on a plane that is parallel to the longitudinal axis of the member.

Additional understanding of the claimed devices and methods can be obtained by reviewing the detailed description of selected examples, below, with reference to the appended drawings.

DETAILED DESCRIPTION OF SELECTED EXAMPLES

The following detailed description and the appended drawings describe and illustrate various example medical devices and methods individually selected by the inventors for the purpose of enabling one skilled in the art to make and use examples of the inventive medical devices and to perform examples of the inventive methods. The examples do not limit the scope of the claims in any manner.

As used herein, the term "lumen," and grammatically related terms, refers to the inside space of a tubular structure. The term does not require any specific dimensions, relative dimensions, configuration, or regularity.

Figure 1:
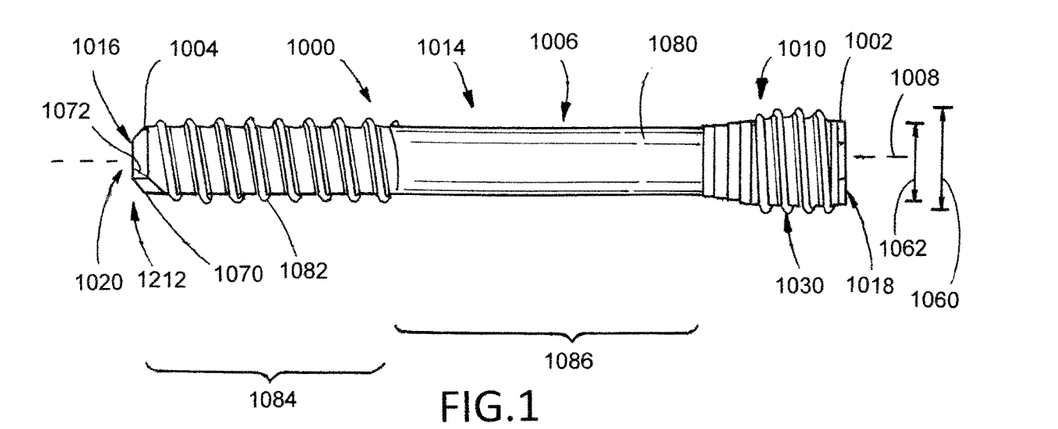
FIG. 1 is a side view of a first example orthopedic screw.
Figure 2:
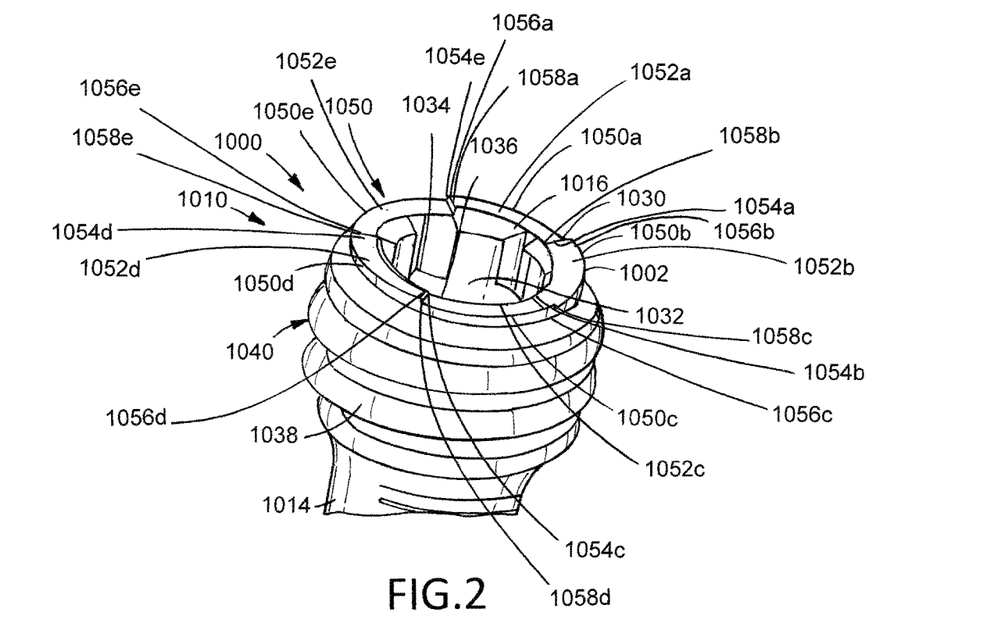
FIG. 2 is a magnified partial perspective view of the first example orthopedic screw. The head portion of the orthopedic screw is illustrated.

FIGS. 1 and 2 illustrate a first example orthopedic screw 1000. The orthopedic screw 1000 has a proximal end 1002, a distal end 1004, and a body 1006 extending between the proximal end 1002 and the distal end 1004 along a longitudinal axis 1008. The orthopedic screw 1000 includes a head portion 1010 that terminates with the proximal end 1002, a tip portion 1012 that terminates with the distal end 1004, and a shaft 1014 extending between the head portion 1010 and the tip portion 1012 and comprising the body 1006. As described in detail below, the tip portion 1012 provides structure for cutting into tissue, such as bone and/or cartilage, and the head portion 1010 provides structure for interacting with one or more tools for placing or implanting the orthopedic screw 1000 into tissue, such as a driver. In this example, the orthopedic screw 1000 defines an inner lumen 1016, allowing it to be passed over a separate member, such as a wire, to facilitate placement and/or positioning during implantation. Accordingly, the orthopedic screw 1000 according to this example is a cannulated screw. It is noted that, while the illustrated example orthopedic screw 1000 is a cannulated screw, orthopedic screws according to other embodiments do not include a lumen, such as solid body orthopedic screws.

In the illustrated example, the proximal end 1002 defines a proximal opening 1018 and the distal end 1004 defines a distal opening 1020. The lumen 1016 extends between the proximal opening 1018 and the distal opening 1020. Thus, each of the proximal opening 1018 and the distal opening 1020 provides access to the lumen 1016 from the environment external to the orthopedic screw 1000. In use, the orthopedic screw 1000 can be passed over a previously-placed wire such that the wire extends through the lumen 1016. The orthopedic screw 1000 can then be advanced over the wire to achieve a desired placement and/or positioning before initiating driving of the orthopedic screw 1000 into tissue. Similarly, a wire can be used during removal of the orthopedic screw 1000 from tissue into which the orthopedic screw 1000 has been implanted. For example, a wire can be placed into the lumen 1016 of the orthopedic screw and advanced distally toward the distal end 1004. A removal tool, such as a driver or other tool, can then be passed over the wire and guided toward to the head portion 1010 to facilitate alignment of the tool and the head portion 1010 prior to application of a removal force.

As best illustrated in FIG. 2, the head portion 1010 has a head core 1030 that defines a cavity 1032 that is bounded by a circumferential wall 1034 and a transverse wall 1036. The circumferential wall 1034 extends around the longitudinal axis 1008 of the orthopedic screw 1000. The transverse wall 1036 transitions the inner diameter of the lumen 1016 from a larger inner diameter of the cavity 1032 to a smaller inner diameter within the body 1006 of the orthopedic screw 1000.

The circumferential wall 1034 defines structure that facilitates interaction with a tool, such as a driver, that can be used to drive the orthopedic screw 1000 into, and remove the screw 1000 from, tissue, such as cartilage and/or bone. The transverse wall 1036 may also define structure that facilitates such interaction. As such, the circumferential wall 1034, the transverse wall 1036, and, as a result, the cavity 1032 may have any suitable configuration and a skilled artisan will be able to select an appropriate configuration for each of these structures in an orthopedic screw according to a particular embodiment based on various considerations, including the configuration and nature of any driver with which the orthopedic screw is intended to be used. Examples of suitable configurations include conventional configurations for screw heads, including hex, star-shaped configurations, such as configurations compatible with TORX brand drivers, and other configurations. In this example, the head 1030 is an enlarged structure relative to the tip portion 1012 and body 1006 of the orthopedic screw.

The external surface 1038 of the head portion 1010 defines head thread 1040. In this example, the head thread 1040 is oriented such that the head thread 1040 cuts into bone into which the orthopedic screw 1000 is being implanted upon application of a clockwise rotational force to the orthopedic screw 1000.

In this example, the circumferential wall 1034 of the head core 1030 defines a series of cutting teeth 1050. The series of cutting teeth 1050 lies on a plane that is perpendicular to the longitudinal axis 1008 of the orthopedic screw 1000. Also, the series of cutting teeth 1050 is oriented in the opposite direction relative to the head thread 1040. Thus, in this example, the series of cutting teeth 1050 is oriented such that the series of cutting teeth 1050 cuts into bone upon application of a counter-clockwise rotational force to the orthopedic screw 1000. The arrangement of the series of cutting teeth 1050 on a plane perpendicular to the longitudinal axis 1008 and in an orientation opposite to that of the head thread 1040 is considered advantageous at least because it places the series of cutting teeth 1050 in a position and orientation suitable for cutting through bone that has grown over the head core 1030 after the orthopedic screw 1000 has been implanted and left in place. As such, this arrangement and orientation facilitates removal of the orthopedic screw 1000.

While the illustrated example includes a head thread 1040 oriented for cutting into bone upon application of a clockwise rotational force and a series of cutting teeth oriented for cutting into bone upon application of a counter-clockwise rotational force, it is noted that, in an embodiment, the orientations of the head thread and series of cutting teeth can be reversed if desired, so long as the opposite nature of these orientations is maintained. Thus, in an embodiment, the head thread can be oriented such that the head thread cuts into bone into which an orthopedic screw according to the embodiment is being implanted upon application of a counter-clockwise rotational force to the orthopedic screw. In this embodiment, the series of cutting teeth would be oriented such that the series of cutting teeth cuts into bone into which an orthopedic screw according to the embodiment is being implanted upon application of a clockwise rotational force to the orthopedic screw.

In the illustrated embodiment, the series of cutting teeth 1050 on the head core 1030 includes five individual cutting teeth 1050a, 1050b, 1050c, 1050d, and 1050e. Each cutting tooth 1050a, 1050b, 1050c, 1050d, and 1050e of the series of cutting teeth 1050 has a curvilinear inclined planar surface 1052a, 1052b, 1052c, 1052d, 1052e that extends from a first end 1054a, 1054b, 1054c, 1054d, 1054e having a first height to a second end 1056a, 1056b, 1056c, 1056d, 1056e having a second height that is greater than the first height. Each cutting tooth 1050a, 1050b, 1050c, 1050d, 1050e of the series of cutting teeth 1050 also has an impact surface 1058a, 1058b, 1058c, 1058d, 1058e that is planar or substantially planar and that extends from the second end 1056a, 1056b, 1056c, 1056d, 1056e of the cutting tooth 1050a, 1050b, 1050c, 1050d, 1050e to the first end 1054a, 1054b, 1054c, 1054d, 1054e of the curvilinear inclined planar surface 1052a, 1052b, 1052c, 1052d, 1052e of the immediately adjacent cutting tooth 1050a, 1050b, 1050c, 1050d, 1050e of the series of cutting teeth 1050. As such, the impact surface 1058a, 1058b, 1058c, 1058d, 1058e of each cutting tooth 1050a, 1050b, 1050c, 1050d, 1050e of the series of cutting teeth 1050 extends from the second end 1056a, 1056b, 1056c, 1056d, 1056e of one cutting tooth 1050a, 1050b, 1050c, 1050d, 1050e of the series of cutting teeth 1050 to the first end 1054a, 1054b, 1054c, 1054d, 1054e of another, immediately adjacent cutting tooth 1050a, 1050b, 1050c, 1050d, 1050e of the series of cutting teeth 1050. Furthermore, the impact surface 1058a, 1058b, 1058c, 1058d, 1058e of each cutting tooth 1050a, 1050b, 1050c, 1050d, 1050e of the series of cutting teeth 1050 transitions from the second height of one cutting tooth 1050a, 1050b, 1050c, 1050d, 1050e of the series of cutting teeth 1050 to the first height of another, immediately adjacent cutting tooth 1050a, 1050b, 1050c, 1050d, 1050e of the series of cutting teeth 1050. In the illustrated embodiment, the impact surface 1058a, 1058b, 1058c, 1058d, 1058e of each cutting tooth 1050a, 1050b, 1050c, 1050d, 1050e of the series of cutting teeth 1050 lies on a plane that contains the longitudinal axis 1008 of the orthopedic screw 1000. It is noted, though, that an orthopedic screw according to a particular embodiment can include one or more cutting teeth that has an impact surface that lies in a plane disposed at an angle to the longitudinal axis of the particular orthopedic screw.

In this embodiment, each cutting tooth 1050a, 1050b, 1050c, 1050d, 1050e of the series of cutting teeth 1050 has the same size and configuration. This number and structural configuration of the cutting teeth in the series of cutting teeth is considered advantageous at least because it provides a desirable number of positions at which cutting action can be initiated along with a regularity to the cutting performance of the series of cutting teeth 1050. It is noted, though, that an orthopedic screw according to a particular embodiment can include any suitable number of individual cutting teeth in a series of cutting teeth, and a skilled artisan will be able select an appropriate number of individual cutting teeth based on various considerations, including the nature of the bone or other tissue into which the orthopedic screw is intended to be implanted, the intended, expected, or potential duration of any implantation period, and any expected likelihood that the orthopedic screw will need to be removed from tissue at a point in time after implantation. The inclusion of five or fewer individual cutting teeth is considered advantageous at least because this number provides an aggressive cutting ability but does not negatively impact the handling characteristics of the orthopedic screw. Examples of numbers of cutting teeth considered suitable for inclusion in an orthopedic screw according to an embodiment include, but are not limited to, one, more than one, multiple, a plurality, two, three, four, five, six, seven, eight, nine, ten, more than ten, a dozen, and multiples of these numbers. It is also noted that an orthopedic screw according to a particular embodiment can include a series of cutting teeth in which at least two individual cutting teeth have different structural configurations. For example, one cutting tooth of the series of cutting teeth can have a curvilinear inclined planar surface that has a first length and a second cutting tooth of the series of cutting teeth can have a curvilinear inclined planar surface that has a second length that is different from the first length. As another example, one cutting tooth of the series of cutting teeth can have a second height at the second end of its curvilinear inclined planar surface, using the identifying terms from the orthopedic screw 1000, that is different from the second height at the second end of the curvilinear inclined planar surface of another cutting tooth of the series of cutting teeth.

As best illustrated in FIG. 1, head thread 1040 has a first outer diameter 1060 at the widest point of the head thread, measured on a plane perpendicular to the longitudinal axis 1008 of the orthopedic screw 1000. The series of cutting teeth 1060 has a second outer diameter 1062, also measured on a plane perpendicular to the longitudinal axis 1008 of the orthopedic screw 1000. The first outer diameter 1060 is different from the second outer diameter 1062. Also as best illustrated in FIG. 1, the first outer diameter 1060 is greater than the second outer diameter 1062; the second outer diameter 1062 is less than the first outer diameter 1060. This structural arrangement is considered advantageous at least because it provides the functional advantage of the series of cutting teeth 1050 but ensures the cutting teeth of the series of cutting teeth 1050 do not interfere with initial insertion of the orthopedic screw 1000 into bone.

The tip portion 1012 defines a tip 1070 at the distal end 1004. The tip 1070 defines cutting edge 1072. Cutting edge 1072 defines structure for cutting into tissue, such as bone and/or cartilage. Cutting edge 1072 may have any suitable configuration and a skilled artisan will be able to select an appropriate configuration for the cutting edge in an orthopedic screw according to a particular embodiment based on various considerations, including the nature of any particular tissue with which the orthopedic screw is intended to be used. Examples of suitable configurations include conventional configurations for bone screw cutting edges. Different configurations may be appropriate for orthopedic screws intended for use in different tissues and/or applications. For example, an orthopedic screw intended for use in fracture fixation in the foot and/or ankle may have one cutting edge configuration while an orthopedic screw intended for us in fracture fixation in the upper extremities may have another, different cutting edge configuration. Orthopedic screws intended for other uses, such as spinal or trauma applications, may have yet other cutting edge configurations.

The shaft 1014 defines external surface 1080 that extends entirely around the longitudinal axis 1008 of the orthopedic screw 1000. As best illustrated in FIG. 1, external surface 1080 defines distal thread 1082. In this example, the distal thread 1080 extends along only a first axial portion 1084 of the shaft 1014, leaving another axial portion 1086 of the shaft 1014 free of the distal thread 1082. It is noted, though, that the distal thread in an orthopedic screw according to a particular embodiment can extend along any suitable axial length of the shaft of the orthopedic screw. A skilled artisan will be able to select a suitable axial length for an orthopedic screw according to an embodiment based on various considerations, including the nature of the bone or other tissue into which the orthopedic screw is intended to be implanted.

The distal thread 1080 can have any suitable structural configuration, and a skilled artisan will be able to select an appropriate configuration for the distal thread in an orthopedic screw according to a particular embodiment based on various considerations, including the nature of any tissue with which the orthopedic screw is intended to be used. One example embodiment, not illustrated, includes sawing teeth which are considered particularly advantageous at least because they provide additional cutting functionality.

Figure 3:
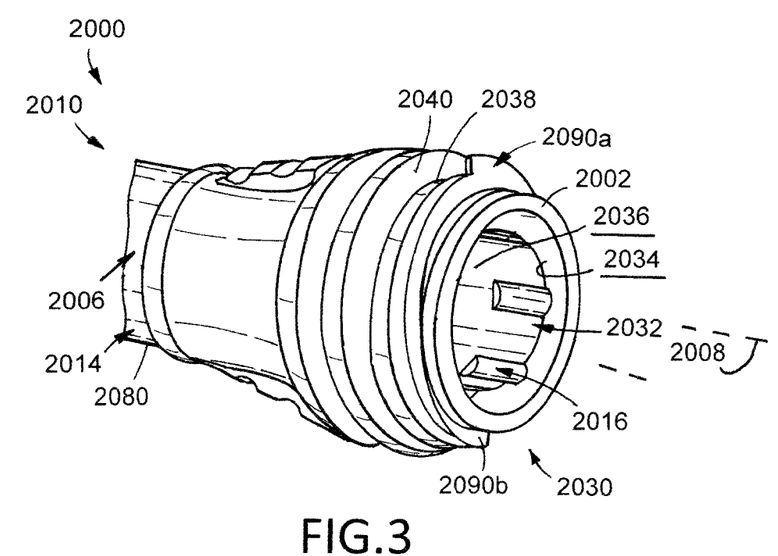
FIG. 3 is a partial perspective view of a second example orthopedic screw. The head portion of the orthopedic screw is illustrated.

FIG. 3 illustrates a second example orthopedic screw 2000. For simplicity, FIG. 3, only illustrates the head portion 2010 and a portion of the shaft 2014 of the orthopedic screw 2000. The orthopedic screw 2000 is identical to the orthopedic screw 1000 described above and illustrated in FIGS. 1 and 2, except as detailed below. Thus, orthopedic screw 2000 has a proximal end 2002, a distal end, and a body extending between the proximal end 2002 and the distal end along a longitudinal axis 2008. The orthopedic screw 2000 includes a head portion 2010 located at the proximal end 2002, a tip portion located at the distal end, and a shaft 2014 extending between the head portion 2010 and the tip portion and comprising the body. The shaft 2014 defines an external surface 2080 that defines a distal thread. The head portion 2010 has a head core 2030 that defines a cavity 2032 that is bounded by a circumferential wall 2034 and a transverse wall 2036. The circumferential wall 2034 extends around the longitudinal axis 2008 of the orthopedic screw 2000. The transverse wall 2036 transitions the inner diameter of the inner lumen 2016 from a larger inner diameter of the cavity 2032 to a smaller inner diameter within the body 2006 of the orthopedic screw 2000. The external surface 2038 of the head portion 2010 defines head thread 2040. In this example, the head thread 2040 is oriented such that the head thread 2040 cuts into bone into which the orthopedic screw 2000 is being implanted upon application of a clockwise rotational force to the orthopedic screw 3000.

In this example, the head thread 2040 defines reverse cutting teeth 2090a, 2090b in the first rotation of the head thread 2040 from the proximal end 2002 of the orthopedic screw 2000. Each of the reverse cutting teeth 2090a, 2090b comprises a step in the flank of the head thread 2040 from the crest of the head thread 2040 to a height between the root of the head thread 2040 and the crest of the head thread 2040.

In the illustrated embodiment, the head thread 2040 includes two individual reverse cutting teeth 2090a, 2090b, each of the same size and configuration. An orthopedic screw according to a particular embodiment can include any suitable number of individual reverse cutting teeth in a series of reverse cutting teeth on the head thread, and a skilled artisan will be able select an appropriate number of individual reverse cutting teeth based on various considerations, including the nature of the bone or other tissue into which the orthopedic screw is intended to be implanted, the intended, expected, or potential duration of any implantation period, and any expected likelihood that the orthopedic screw will need to be removed. The inclusion of two or fewer individual reverse cutting teeth is considered advantageous at least because this number provides an aggressive cutting ability but does not negatively impact the ability of the head thread to cut into bone upon initial implantation.

Also in this embodiment, the circumferential wall 2034 of the head core 2030 comprises a continuous circumferential flange that forms the proximal end 2002 of the orthopedic screw 2000. As such, and in contrast to the first example orthopedic screw 1000 described above and illustrated in FIGS. 1 and 2, the circumferential wall 2034 of the head core 2030 in this embodiment does not define any cutting teeth.

Figure 4:
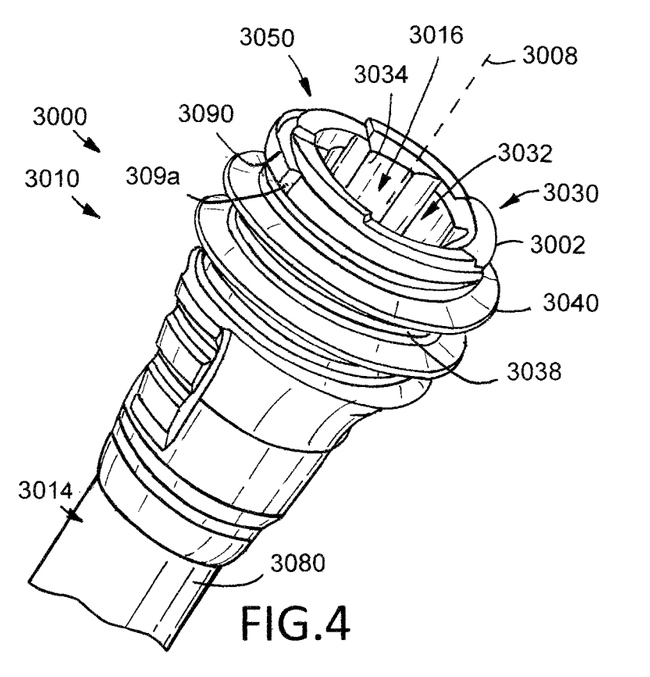
FIG. 4 is a partial perspective view of a third example orthopedic screw. The head portion of the orthopedic screw is illustrated.

FIG. 4 illustrates a third example orthopedic screw 3000. For simplicity, FIG. 4, only illustrates the head portion 3010 and a portion of the shaft 3014 of the orthopedic screw 3000. The orthopedic screw 3000 is similar to the orthopedic screw 2000 described above and illustrated in FIGS. 1 and 2, except as detailed below. Thus, orthopedic screw 3000 has a proximal end 3002, a distal end, and a body extending between the proximal end 3002 and the distal end along a longitudinal axis 3008. The orthopedic screw 3000 includes a head portion 3010 located at the proximal end 3002, a tip portion located at the distal end, and a shaft 3014 extending between the head portion 3010 and the tip portion and comprising the body. The shaft 3014 defines an external surface 3080 that defines a distal thread. The head portion 3010 has a head core 3030 that defines a cavity 3032 that is bounded by a circumferential wall 3034 and a transverse wall. The circumferential wall 3034 extends around the longitudinal axis 3008 of the orthopedic screw 3000. The transverse wall transitions the inner diameter of the lumen 3016 from a larger inner diameter of the cavity 3032 to a smaller inner diameter within the body 3006 of the orthopedic screw 3000. The external surface 3038 of the head portion 3010 defines head thread 3040. In this example, the head thread 3040 is oriented such that the head thread 3040 cuts into bone into which the orthopedic screw 3000 is being implanted upon application of a clockwise rotational force to the orthopedic screw 3000.

In this example, the head thread 3040 defines a single reverse cutting tooth 3090 in the first rotation of the head thread 3040 from the proximal end 3002 of the orthopedic screw 3000. The reverse cutting tooth 3090 comprises a step in the flank of the head thread 3040 from the crest of the head thread 3040 to the root of the head thread 3040 and the crest of the head thread 3040.

The orthopedic screw 3000 also includes a series of cutting teeth 3050 on the circumferential wall 3034 of the head core 3030. The series of cutting teeth 3050 lies on a plane that is perpendicular to the longitudinal axis 3008 of the orthopedic screw 3000. Also, the series of cutting teeth 3050 is oriented in the opposite direction relative to the head thread 3040. Thus, in this example, the series of cutting teeth 3050 is oriented such that the series of cutting teeth 3050 cuts into bone upon application of a counter-clockwise rotational force to the orthopedic screw 3000. In this example, the series of cutting teeth 3050 is similar to the series of cutting teeth 1050 described above and illustrated in FIGS. 1 and 2 in connection with the first example orthopedic screw 1000.

In the illustrated embodiment, reverse cutting tooth 3090 includes an impact surface 3090a that lies on a plane disposed between first and second planes on which first and second impact surfaces of first and second teeth of the series of cutting teeth 3050. This structural configuration is considered advantageous at least because it ensures a distance between impact surfaces of the reverse cutting tooth 3090 and the impact surfaces of the cutting teeth of the series of cutting teeth 3050. It is noted, though, that an orthopedic screw according to a particular embodiment can include a reverse cutting tooth having an impact surface that lies on a plane on which an impact surface of a cutting tooth of the series of cutting teeth also lies.

The inclusion of both the reverse cutting tooth 3090 in the head thread 3040 and the series of cutting teeth 3050 on the circumferential wall 3034 of the head core 3030 is considered advantageous at least because it provides multiple structures to interface with and disrupt bone overgrowth to facilitate removal of the orthopedic screw 3000 from bone after implantation. Furthermore, the inclusion of both a cutting tooth, or multiple cutting teeth, that is or are defined by a thread that extends along a spiral path around the longitudinal axis of the orthopedic screw, such as cutting tooth 3090 in the head thread 3040, and a series of cutting teeth that lies on a plane that is perpendicular to the longitudinal axis the orthopedic screw, such as series of cutting teeth 3050, is considered advantageous at least because it provides multiple modes of action for interfacing with and disrupting bone overgrowth to facilitate removal of the orthopedic screw from bone after implantation.

Figure 5:
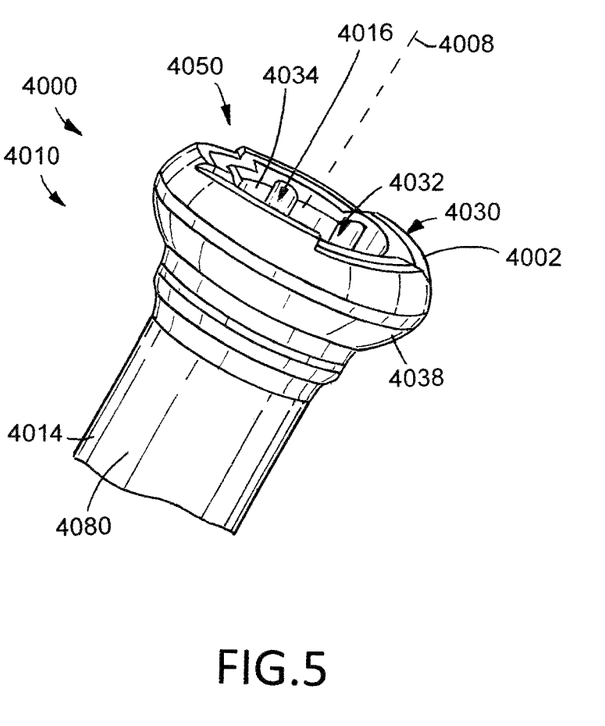
FIG. 5 is a partial perspective view of a fourth example orthopedic screw. The head portion of the orthopedic screw is illustrated.

FIG. 5 illustrates a fourth example orthopedic screw 4000. For simplicity, FIG. 5, only illustrates the head portion 4010 and a portion of the shaft 4014 of the orthopedic screw 4000. The orthopedic screw 4000 is similar to the orthopedic screw 1000 described above and illustrated in FIGS. 1 and 2, except as detailed below. Thus, orthopedic screw 4000 has a proximal end 4002, a distal end, and a body extending between the proximal end 4002 and the distal end along a longitudinal axis 4008. The orthopedic screw 4000 includes a head portion 4010 located at the proximal end 4002, a tip portion located at the distal end, and a shaft 4014 extending between the head portion 4010 and the tip portion and comprising the body. The shaft 4014 defines an external surface 4080 that defines a distal thread. The head portion 4010 has a head core 4030 that defines a cavity 4032 that is bounded by a circumferential wall 4034 and a transverse wall. The circumferential wall 4034 extends around the longitudinal axis 4008 of the orthopedic screw 4000. The transverse wall transitions the inner diameter of the inner lumen 4016 from a larger inner diameter of the cavity 4032 to a smaller inner diameter within the body 4006 of the orthopedic screw 4000.

In this example, the orthopedic screw 4000 also includes a series of cutting teeth 4050 on the circumferential wall 4034 of the head core 4030. The series of cutting teeth 4050 lies on a plane that is perpendicular to the longitudinal axis 4008 of the orthopedic screw 4000. Also, the series of cutting teeth 4050 is oriented such that the series of cutting teeth 4050 cuts into bone upon application of a counter-clockwise rotational force to the orthopedic screw 4000.

In this example, the external surface 4038 of the head portion 4010 defines a smooth surface that is free of a thread. Indeed, in this example, the orthopedic screw 4000 only includes a single thread on the distal end.

In all embodiments, the orthopedic screw can be made of any material suitable for use in medical devices intended for orthopedic use, including use as a long-term implant. Examples of suitable materials include metals, metal alloys, and polymeric materials. Examples of suitable metals include, but are not limited to, Titanium, Magnesium, and other metals. Examples of suitable metal alloys include, but are not limited to, Ti6Al4V, 316 LVM, 1.4441Ti-13Nb-13Zr, Ti-12Mo-6Zr-2Fe, Ti-15Mo-5Zr-3Al, Ti-15Mo, Ti-35Nb-7Zr-5Ta and Ti-29Nb-13Ta-4.6Zr Ti-6Al-7Nb and Ti-15Sn-4Nb-2Ta-0.2Pd Co—Cr—Mo alloys. Examples of suitable polymeric materials include, but are not limited to, polyaryletherketone (PAEK), polyether ether ketone (PEEK), PEEK (90G, 450G, I2, I4), Polyamide, PA66, carbon fiber reinforced polyaryletherketone (CFR PAEK), polyether ketone ketone (PEKK), carbon fiber reinforced polyether ketone ketone (CFR PEKK), carbon fiber reinforced polyether ether ketone (CFR PEEK), CFR PEEK (90G CA30, 90G CA20, 450G CA30, 450G CA20, I2 CF20, I2 CF30, I4 CF30, I4 CF20), Polyamide CFR, and PA66 CFR.

Orthopedic screws according to some embodiments include multiple components, such as an inner core member and an outer body member. In these embodiments, the components can be formed of the same or different materials. For example, an orthopedic screw according to an embodiment can include an inner core member that defines a distal tip, head core, and a series of cutting teeth on the head core as described above, and an outer body member that circumferentially surrounds the inner core member and defines a distal thread and a head thread. In this embodiment, it is considered advantageous to include an inner core member formed of a first metallic material, such as a metal or a metal alloy, and an outer body member formed of a second, different material, such as a polymeric material, a blended material such as a carbon fiber reinforced polymer, or another non-metallic material. It is considered particularly advantageous to include an inner core member formed of a Titanium alloy, such as Ti6Al4V, and an outer body member formed of a second, different material, such as CFR PEEK at least because this combination of materials provides desirable characteristics and a favorable balance between manufacturability and strength considerations. In these embodiments, the outer body member can be made of any material suitable for use in medical devices intended for orthopedic use, including use as a long-term implant. Examples of suitable types of materials include, but are not limited to, polymeric materials, blended materials such as carbon fiber reinforced polymers, and other materials. Examples of suitable polymeric materials include, but are not limited to, PAEK, CFR PAEK, PEKK, CFR PEKK, PEEK, CFR-PEEK, PEEK (90G, 450G, I2, I4), Polyamide, and PA66. Examples of suitable blended materials include, but are not limited to, PEEK-Carbon materials, CFR PAEK, CFR PEKK, CFR PEEK (90G CA30, 90G CA20, 450G CA30, 450G CA20, I2 CF20, I2 CF30, I4 CF30, I4 CF20), Polyamide CFR, PA66 CFR.

It is noted that the materials used in an orthopedic screw according to a particular embodiment can include additives, coatings, fillers, and/or other elements if desired. For example, antibiotics, bioactive glass, silver, copper, or another material that can reduce bacterial colonization of the orthopedic screw following implantation can be included in the material of the inner core member, the outer body member, or both.

Figure 6:
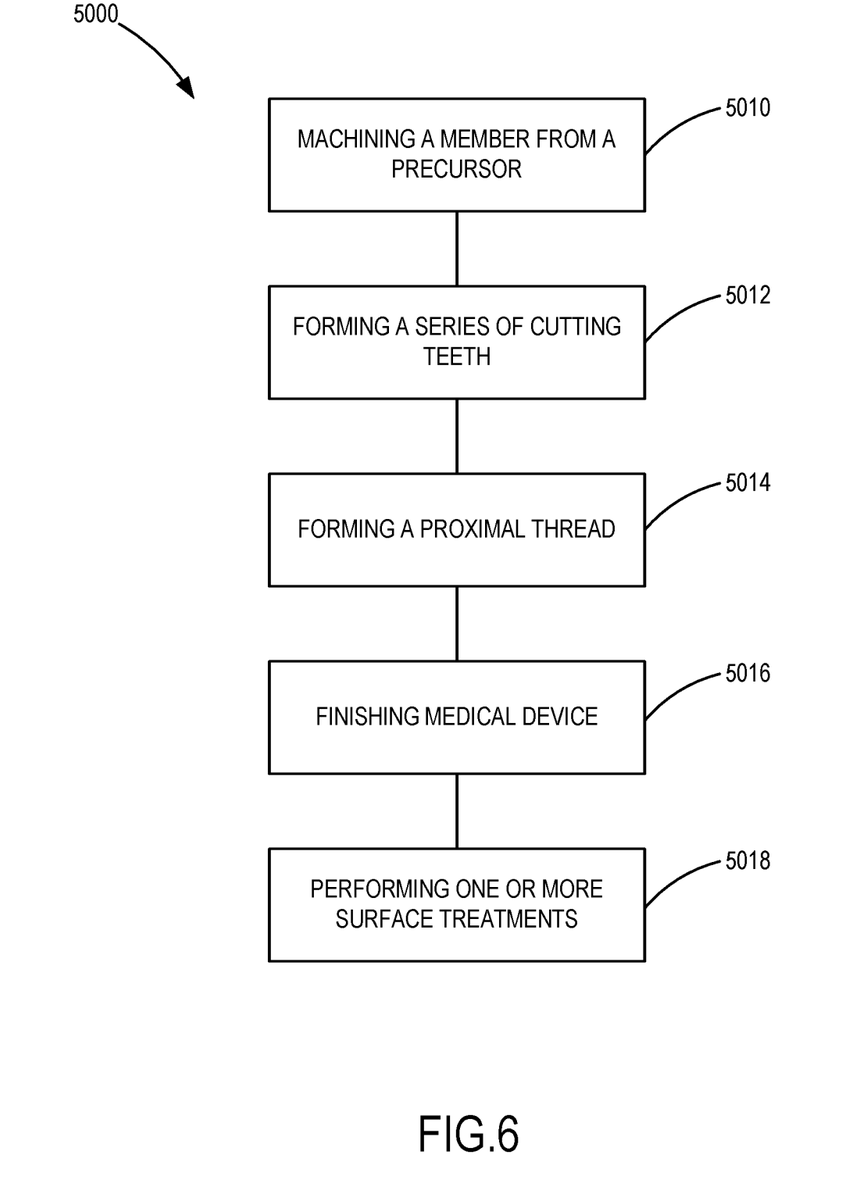
FIG. 6 is a flowchart representation of a first example method of manufacturing an orthopedic screw.

FIG. 6 is a schematic representation of a method 5000 of manufacturing an orthopedic screw. A step 5010 comprises machining a member from a suitable precursor, such as a solid rod or cannula to form a distal thread on an external surface of the member between proximal and distal ends of the member. Another step 5012 comprises forming a series of cutting teeth on the proximal end of the member such that the series of cutting teeth lies on a plane that is parallel to the longitudinal axis of the member. An optional step 5014 comprises forming a proximal thread on the external surface of the member at an axial position between the distal thread and the proximal end of the member. Additional steps, such as step 5016, which comprises finishing the medical device using suitable techniques or processes, can also be included. Another additional step 5018 comprises performing one or more surface treatments on the medical device, such as roughening, coating, and the like.

Figure 7:
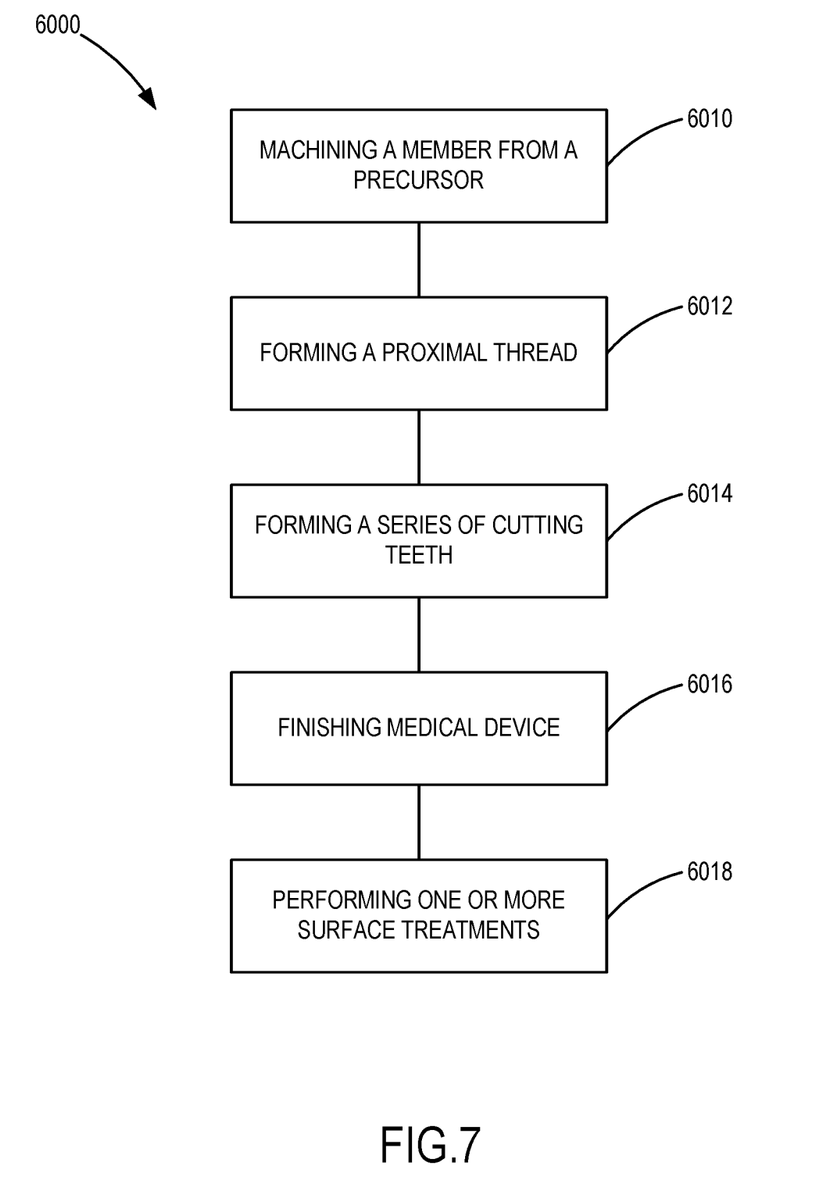
FIG. 7 is a flowchart representation of a second example method of manufacturing an orthopedic screw.

FIG. 7 is a schematic representation of another method 6000 of manufacturing an orthopedic screw. A step 6010 comprises machining a member from a suitable precursor, such as a solid rod or cannula to form a distal thread on an external surface of the member between proximal and distal ends of the member. Another step 6012 comprises forming a proximal thread on the external surface of the member at an axial position between the distal thread and the proximal end of the member such that the proximal thread includes a reverse cutting tooth in the first rotation of the proximal thread. An optional step 6014 comprises forming a series of cutting teeth on the proximal end of the member such that the series of cutting teeth lies on a plane that is parallel to the longitudinal axis of the member. Additional steps, such as step 6016, which comprises finishing the medical device using suitable techniques or processes, can also be included. Another additional step 6018 comprises performing one or more surface treatments on the medical device, such as roughening, coating, and the like.

Those with ordinary skill in the art will appreciate that various modifications and alternatives for the described and illustrated examples can be developed in light of the overall teachings of the disclosure, and that the various elements and features of one example described and illustrated herein can be combined with various elements and features of another example without departing from the scope of the invention. Accordingly, the particular examples disclosed herein have been selected by the inventors simply to describe and illustrate examples of the invention are not intended to limit the scope of the invention or its protection, which is to be given the full breadth of the appended claims and any and all equivalents thereof.

We claim:

1. An orthopedic screw, comprising:
   a head portion defining a proximal end, a tip portion defining a cutting edge and a distal end, the tip portion defining the distal end, a body extending between the proximal end and the distal end along a longitudinal axis and defining a distal thread extending around the longitudinal axis;
   the head portion defining a circumferential wall and a cavity, the circumferential wall bounding the cavity and extending around the longitudinal axis, the head portion terminating in an end surface that extends along a plane that is perpendicular to the longitudinal axis, the end surface defining a series of cutting teeth of varying height, each tooth projecting outwardly away from the end surface in a direction along the longitudinal axis and adapted for cutting through bone that has grown over the head portion; and
   wherein the proximal end defines a proximal opening communicating with the cavity.

2. The orthopedic screw of claim 1, wherein the head portion defines a proximal thread extending around the longitudinal axis and disposed between the distal thread and the proximal end.

3. The orthopedic screw of claim 2, wherein the proximal thread defines a reverse cutting tooth in the first rotation of the proximal thread relative to the proximal end.

4. The orthopedic screw of claim 2, wherein the proximal thread defines a series of reverse cutting teeth in the first rotation of the proximal thread relative to the proximal end.

5. The orthopedic screw of claim 2, wherein the proximal thread has a first outer diameter and the proximal end has a second, different outer diameter.

6. The orthopedic screw of claim 5, wherein the first outer diameter is greater than the second outer diameter.

7. The orthopedic screw of claim 1, wherein an inner core member defines the tip portion and the series of cutting teeth; and
   further comprising an outer body member disposed circumferentially around the inner core member and comprising the body.

8. The orthopedic screw of claim 7, wherein the inner core member is formed of a first material and the outer body member is formed of a second, different material.

9. The orthopedic screw of claim 8, wherein the first material comprises a metal.

10. The orthopedic screw of claim 9, wherein the second material comprises a polymeric material.

11. The orthopedic screw of claim 7, wherein the head portion defines a proximal thread extending around the longitudinal axis and disposed between the distal thread and the proximal end.

12. An orthopedic screw, comprising:
    a shaft having a proximal end, a distal end, a body extending between the proximal end and the distal end along a longitudinal axis, the shaft having a shaft external surface defining a distal thread extending around the longitudinal axis;
    a head portion on the shaft, the head portion defining a proximal thread, a circumferential wall, and a cavity, the circumferential wall bounding the cavity and extending around the longitudinal axis, the head portion terminating in an end surface that extends along a plane that is perpendicular to the longitudinal axis of the shaft, the end surface defining a series of cutting teeth of varying height, each tooth projecting outwardly away from the end surface in a direction along the longitudinal axis and adapted for cutting through bone that has grown over the head portion, the proximal thread disposed between the distal thread and the series of cutting teeth and extending around the longitudinal axis; and a tip portion on the shaft, the tip portion defining a cutting edge wherein the tip portion defines the distal end;

wherein the proximal thread has a first outer diameter and the proximal end has a second outer diameter that is less than the first outer diameter.

13. The orthopedic screw of claim 12, wherein the proximal thread defines a reverse cutting tooth in the first rotation of the proximal thread relative to the proximal end.

14. The orthopedic screw of claim 12, wherein the proximal thread defines a series of reverse cutting teeth in the first rotation of the proximal thread relative to the proximal end.

15. An orthopedic screw, comprising:

an inner core member defining a proximal end, a distal end, and a body extending between the proximal end and the distal end along a longitudinal axis, the proximal end defining a circumferential wall and a cavity, the circumferential wall bounding the cavity and extending around the longitudinal axis, on the proximal end terminating in an end surface that extends along a plane that is perpendicular to the longitudinal axis, the end surface defining a series of cutting teeth of varying height, each tooth projecting outwardly away from the end surface in a direction along the longitudinal axis and adapted for cutting through bone that has grown over the head portion, the distal end defining a cutting edge; and an outer body member disposed circumferentially around the inner core member and defining a distal thread extending around the longitudinal axis.

16. The orthopedic screw of claim 15, wherein the outer body member further defines a proximal thread extending around the longitudinal axis and disposed between the distal thread and the proximal end.

17. The orthopedic screw of claim 16, wherein the proximal thread defines a reverse cutting tooth in the first rotation of the proximal thread relative to the proximal end.

18. The orthopedic screw of claim 15, wherein the inner core member is formed of a first material and the outer body member is formed of a second, different material.

19. The orthopedic screw of claim 18, wherein the first material comprises a metal.

20. The orthopedic screw of claim 19, wherein the second material comprises a polymeric material.

* * * * *

UNITED STATES PATENT AND TRADEMARK OFFICE
CERTIFICATE OF CORRECTION

| | |
|---|---|
| PATENT NO. | : 10,939,944 B2 |
| APPLICATION NO. | : 16/387799 |
| DATED | : March 9, 2021 |
| INVENTOR(S) | : Peter William Wapner et al. |

Page 1 of 1

It is certified that error appears in the above-identified patent and that said Letters Patent is hereby corrected as shown below:

In the Claims

Column 13, Claim 15, Line 18 delete:
"axis, on the proximal"
To:
--axis, the proximal--

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*